United States Patent

Stein et al.

[11] Patent Number: 5,842,373
[45] Date of Patent: Dec. 1, 1998

[54] SINGLE FIBER TESTING DEVICE

[75] Inventors: Wolfgang Stein; Alex Mörschel, both of Mönchengladbach, Germany

[73] Assignee: Textechno Herbert Stein GmbH & Co. KG, Germany

[21] Appl. No.: 735,304

[22] Filed: Oct. 16, 1996

[30] Foreign Application Priority Data

Dec. 8, 1995 [DE] Germany ............... 295 19 501 U

[51] Int. Cl.⁶ ............................................. G01L 5/04
[52] U.S. Cl. ............................................. 73/160; 73/826
[58] Field of Search ............... 73/159, 160, 828, 73/829, 830, 826, 866, 865.8, 862.391, 862.392, 862.393; 340/677, 675; 250/548, 559, 571; 242/36, 49, 357, 534, 563

[56] References Cited

U.S. PATENT DOCUMENTS

| | | | |
|---|---|---|---|
| 3,969,930 | 7/1976 | Prevorsek | 73/826 |
| 5,138,879 | 8/1992 | Shofner | 73/160 |
| 5,269,181 | 12/1993 | Gibson | 73/160 |

*Primary Examiner*—Christine K. Oda
*Attorney, Agent, or Firm*—Brian M. Dingman

[57] ABSTRACT

A device for the testing of single fibers (1), comprising a testing zone (2) for tensile testing between a stationary measuring clamp (3) and a movable draw-off clamp (4), is characterized in that at least one measuring head (8) of a further measuring device for at least one further testing process to be performed simultaneously or successively, is arranged in or adjacent the testing zone (2).

10 Claims, 3 Drawing Sheets

SINGLE FIBER TESTING DEVICE

BACKGROUND OF THE INVENTION

The present invention relates to a device for the testing of single fibers according to the preamble of the main claim.

Such devices are used, e.g., for performing a tensile test on single fibers. For this purpose, the fiber is clamped into a measuring clamp and a draw-off clamp and is then subjected to an increasing tensile stress by moving the draw-off clamp relative to the measuring clamp and away from the latter. The thus generated tensile force acts on a force measuring unit via the measuring clamp.

Tensile testing devices of the above type serve for detecting the maximum tensile force, the elongation resulting from the maximum tensile force and the development of the stress/strain curve.

For these tensile testing processes, preferred use is made of tensile testing devices operating after the principle of constant elongation speed with electronic force measurement. A known device of this type is distributed by the company Textechno, Mönchengladbach/Germany, under the product name FAFEGRAPH (a tensile single fiber testing device). In this device, a single fiber held between the clamps is subjected to a tensile test with a constant draw-off speed. The measuring clamp and the draw-off clamp are pneumatically operated. This device may also be used with measuring and draw-off clamps which take up a bundle of single fibers.

For other destruction-free measurements to be performed on a single fiber, it is required to use a different device. This causes the disadvantage that either the testing is not performed on the same single fiber which is subjected to the tensile test, or the same single fiber has to be arranged and tested in different devices after each testing and then has to be transported by hand each time, which means that damage to the fiber and impairment of the measurement results cannot be ruled out. A further disadvantage is caused by the relatively large time requirements of such an approach.

SUMMARY OF THE INVENTION

It is an object of the invention to improve a device for the testing of single fibers of the above type in such a manner that, in case of different testing processes, an impairment of the measurement results is prevented and that the time and operating requirements of the testing are reduced.

The above object is solved by the features of claim 1.

According to the invention, it is advantageously provided that at least one further measuring head of a further measuring device for at least one testing process to be performed simultaneously or successively, is arranged in or adjacent the testing zone for the tensile test. Thus, the inventive single fiber testing device makes it possible to perform not only a tensile test but also other tests on the same single fiber. This offers the considerable advantage that the measurement results of different tests relate respectively to the same single fiber. Further, this feature allows for a better assignment of the interactions between the fiber parameters obtained by the tests.

In one embodiment, it is provided that said at least one further measuring head is either fixedly installed in the testing zone or is to be positioned into the testing zone by a shifting or pivoting means. Since the further test is carried out in the same testing zone, it is not required anymore that the fiber is newly clamped into position and newly subjected to a pretension weight, thus reducing the risk of damage to the fiber when manipulating the single fiber.

In an alternative embodiment, it is provided that a pivotable and/or shiftable auxiliary clamp will supply the fiber first to said further measuring head, which is arranged separately from the tensile testing zone, and—after the respective measuring process has been performed on the single fiber—will place the fiber into the testing zone for the tensile test. This alternative embodiment will be used in cases in which the provided second testing process cannot be performed in the testing zone for tensile testing.

In a preferred embodiment, it is provided that said further measuring head will measure the fineness of the single fiber by causing the single fiber to perform transverse oscillations and by determining the resonance frequency of the fiber. Such a combined measurement performed on single fibers is time- and cost-saving and further allows for the calculation of fineness-related tenacity values.

In this regard, it can be provided that an acoustic device, e.g. a loudspeaker, excites the to-be-tested single fiber to perform transverse oscillations. The resonance frequency of the fiber can be detected by changing the tone frequency of the acoustic device.

Preferably, a linear photoelectric sensor, arranged transverse to the fiber and combined with a light source directed onto said photoelectric sensor and emitting parallelized light, is provided to detect the transverse oscillations of the single fiber between the photoelectric sensor and the light source. The photoelectric sensor generates a signal depending on the position of the single fiber so that the oscillation of the single fiber can be analyzed.

By way of alternative, the fineness of the single fiber can be measured also by determination of the mass in the electric field, by use of optical means, or by measuring the flow resistance in an air stream.

Said further measuring head can be also used to measure the outer structure of the single fiber, e.g. the crimp of the fiber, by optical means. This process can of course be performed in combination with the fineness measurement according to all of the above mentioned methods. For instance, the fiber crimp can be measured—as in the fineness measurement—using a light source directed onto the photoelectric sensor and emitting parallelized light. In this case, the single fiber is arranged between the light source and the photoelectric sensor, with the light source and the photoelectric sensor being adapted for displacement along the testing zone.

The photoelectric sensor can comprise a position-sensing photodetector, e.g. a lateral-effect photodiode, provided to receive the light of a light source—which light has been parallelized e.g. by a collimator—and to generate a varying measuring signal according to the position of the single fiber.

Preferably, relative to the single fiber placed in the testing zone, the light source is arranged towards the inside, i.e. towards the instant device, while the photoelectric sensor is arranged towards the outside, i.e. on the side opposite to the light source. Since the photoelectric sensor is arranged towards the device, impaired measuring results caused by interfering light from other light sources can be excluded.

Said further measuring head can also be used for measuring the inner structure of the single fiber, e.g. by optical means or by measuring the propagation speed of longitudinal waves. Also this testing process can be performed in combination with the above mentioned tests.

Embodiments of the invention will be explained in greater detail hereunder with reference to the accompanying drawings.

DETAILED DESCRIPTION OF THE INVENTION

Figure 1:
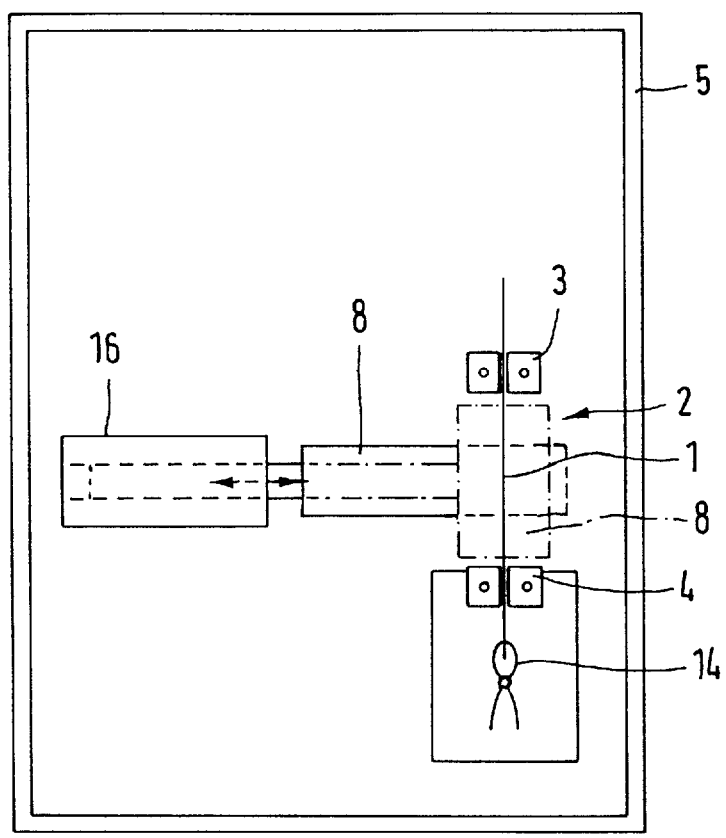
FIG. 1 shows an embodiment of the single fiber testing device together with a movable measuring head of an additional measuring device.

In the testing device illustrated in FIG. 1, single fibers can be subjected to a combinatory testing for maximum tensile force, elongation resulting from maximum tensile force etc., performed in combination with other tests, e.g. tests for detecting the fineness of the single fiber and/or the inner or outer structure of the single fiber.

The measuring devices are integrated into a common housing 5.

The tensile testing device, known per se, comprises a stationary measuring clamp 3 connected to a load cell, and a movable draw-off clamp 4. On the basis of the moving distance covered by draw-off clamp 4, the elongation of the single fiber can be measured.

The single fiber to tested is either manually or automatically placed into the testing zone 2 extending between the stationary measuring clamp 3 and the movable draw-off clamp 4, the lower end of the fiber having attached thereto a weight 14 determining the pretension of the fiber. With the measuring clamp 3 and the draw-off clamp 4, a usual tensile testing process can be carried out. By way of alternative to said pretension weight hanging down from the fiber, the pretension of the fiber can be by generated by a first elongation with simultaneous measurement of the tensile force in the fiber.

Figure 2:
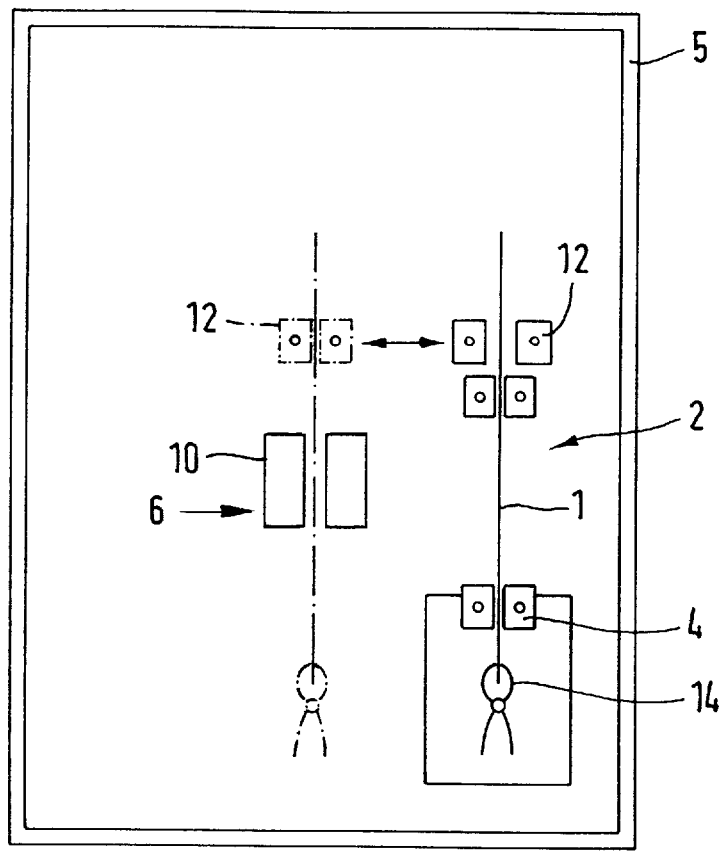
FIG. 2 shows the arrangement of a further measuring head in a second testing zone adjacent to the testing zone for tensile tests.
Figure 3:
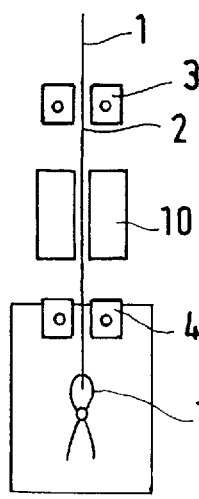
FIG. 3 shows an embodiment of the single fiber testing device together with a further measuring head belonging to an additional measuring device and integrated into the testing zone for tensile tests.
Figure 4:
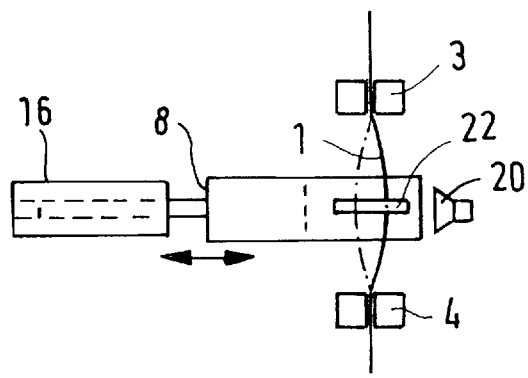
FIG. 4 shows an embodiment of a further measuring head for fineness measurement with acoustic excitement of the single fiber to perform transverse oscillations.
Figure 5:
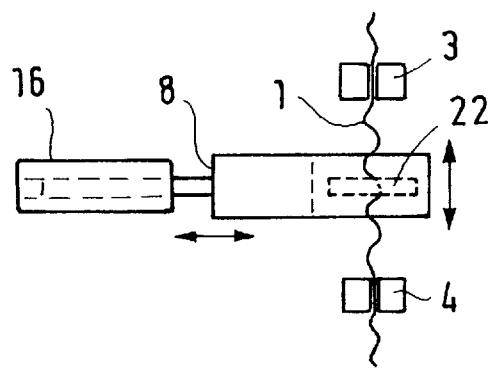
FIG. 5 shows the use of a further measuring head for crimp measurement.
Figure 6:
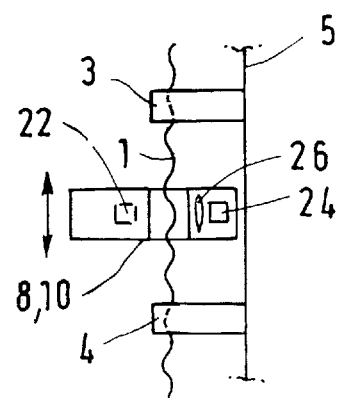
FIG. 6 is a side view of the embodiment according to FIG. 5.

A further measuring head 8,10 of a further measuring device is arranged either to be displaced according to FIG. 1 into the testing zone 2 in a linear direction or along a predetermined moving curve by an operating means 16, or is arranged according to FIG. 2 beside the testing zone 2, or is arranged according to FIG. 3 within the testing zone 2. The measuring head 8,10 of said further measuring device can be used for performing—simultaneously or successively—at least one further test process in the testing zone 2,6.

FIG. 2 illustrates an alternative embodiment wherein, above the measuring clamp 3 of the tensile testing device, an auxiliary clamp 12 is arranged to take over the single fiber 1 from a second testing zone 6, arranged e.g. in parallel with the first testing zone 2, and to feed the single fiber 1 to the tensile testing device. Within the second testing zone 6, a measuring head 10 of a further measuring device is arranged.

Said further measuring heads 8,10 can be provided to measure the fineness of the single fiber 1 by causing transverse oscillations of the single fiber or be detecting the resonance frequency of the single fiber.

The automatic detection of the fineness of a single fiber 1 is performed according to the oscillation method. First, in this measuring method, the resonant frequency of the single fiber is measured for a known testing zone length and a known pretension weight, and the fineness is calculated from the thus obtained measuring values. To measure the resonant frequency of the fiber, two different measuring methods can be employed. In both of these methods, the single fiber 1 is caused to perform a transverse oscillation through an acoustic device 20, e.g. a sound transducer. This oscillation will then be detected in a direction transverse of the single fiber 1 by a linear optoelectronic photoelectric sensor 22 arranged transverse to the fiber.

In the frequency interval method, the single fiber 1 is excited to oscillate by use a sinusoidal sound wave, and the oscillation amplitude of the single fiber 1 is measured. By stepwise changes of the excitation frequency and a respective renewed measurement of the oscillation amplitude, the frequency-dependent development of the amplitude over the relevant frequency range, e.g. from 1 to 2.5 kHz, is picked up. That excitation frequency which results in the maximum oscillation amplitude is the resonant frequency of the single fiber 1.

To accelerate this relatively time-consuming measuring method, a first measurement will aim only at a rough detection of the resonant frequency. The first measurement is followed by a second measurement with higher resolution, performed in a narrower frequency interval. The overall measurement period is only about 5 to 6 secs.

In the pulse method, provided as an alternative, the resonant frequency of the single fiber 1 is first detected only roughly, as is the case in the above frequency interval method. Subsequently, the excitation frequency is adjusted to this resonant frequency. Thereafter, the excitation is stopped, and the oscillation behavior of the fiber is examined. The oscillation frequency of the single fiber will correspond to its resonant frequency.

Alternatively, the fineness of the single fiber can be measured also by determination of the mass in the electric field, by use of optical means, or by measuring the flow resistance in an air stream.

The measuring head 8,10 provided for optic measurement is also suited for measuring the outer structure of the single fiber, e.g. the fiber crimp. The same measuring head 8,10 which is used for fineness measurement can be employed also for automatic measurement of the crimp geometry of the single fiber. In doing so, the linear photoelectric sensor 22 arranged transverse to the single fiber is moved together with the measuring head 8,10 along the testing zone 2,6, and the signal of photoelectric sensor 22 is processed into a digital image of the fiber which is suited for evaluation of the number of the crimp curves, the crimp curve amplitude, and coefficients of measure for the irregularity of these two characteristic quantities.

The photoelectric sensor 22 preferably comprises a position-sensing photodetector, e.g. a lateral-effect photodiode, cooperating with a light source 24 arranged opposite to the lateral-effect photodiode. The light rays of light source 24 are parallelized by a collimator 26. Light source 24 generates a shadow image on the lateral-effect photodiode which, corresponding to the deviation of the position of the respectively detected element of the single fiber 1 relative to the clamping plane defined by the holding clamps 2,4, will generate a varying position signal.

For intensifying this effect, the lateral-effect photodiode, designed as a position-sensitive linear sensor, can be additionally provided with an aperture whose opening width is variable in the longitudinal direction of the linear sensor. In combination with the lateral-effect photodiode, the triangular aperture intensifies the variation of the signal over the width.

The triangular aperture is also useful when arranged before a normal photocell provided as a linear sensor, since also this arrangement will provide for a dependency from the position of the shadow.

When the fineness measurement or the crimp measurement function has been activated, the single fiber 1 is arranged between photoelectric sensor 22 and light source 24. When performing fineness measurement, the measuring head 8,10 is in a suitable position for allowing the detection of the maximum oscillation amplitude of the single fiber 1, i.e. in a position midway along the testing zone 2,6. When performing crimp measurement, on the other hand, the measuring head is reciprocated in the longitudinal direction of the single fiber 1 for scanning the crimp structure.

Preferably, the light source 24 is arranged orthogonally to the single fiber 1 on the side of measuring head 8,10 facing towards housing 5, and the opposite photoelectric sensor 22 is arranged on the side of measuring head 8,10 facing away from housing 5. In this manner, the influence of interfering external light is minimized.

Further, also the inner structure of the single fiber can be measured, e.g. by optical means or by measuring the propagation speed of longitudinal waves.

We claim:

1. A device for testing a single fiber (1) comprising: a testing zone (2) for tensile testing processes between a stationary measuring clamp (3) and a movable draw-off clamp (4), characterized in that at least one measuring head (8,10) is arranged in or adjacent the testing zone (2), and said at least one measuring head (8,10) is provided to measure the fineness of the single fiber (1) by causing the single fiber (1) to perform transverse oscillations and by determining the resonance frequency of the single fiber.

2. The device according to claim 1 wherein said at least one can be measuring head (8,10) is shifted or pivoted into the testing zone (2).

3. The device according to claim 1 wherein an acoustic device (20) is provided for causing the to-be-tested single fiber (1) to perform transverse oscillations.

4. The device according to claim 1 wherein a linear photoelectric sensor (22) is provided in combination with a light source (24) for parallelized light directed onto the photoelectric sensor (22), to detect the transverse oscillations of the single fiber (1) between the photoelectric sensor (22) and the light source (24).

5. The device according to claim 4 wherein said linear photoelectric sensor (22) and said light source (24) for parallelized light directed onto the photoelectric sensor (22), which are arranged to receive the to-be-tested fiber (1) between them, are moved along the testing zone (2,6).

6. The device according to claim 5 wherein the photoelectric sensor (22) is a position-sensing photodetector, generating an output signal according to the position of the shadow of the fiber.

7. The device according to claim 5 wherein an aperture (26) widened in one oscillation direction of the single fiber (1) is arranged before the photoelectric sensor (22) in a manner providing also for a dependency from the position of the shadow.

8. The device according to claim 4 wherein, relative to the single fiber (1) placed in the testing zone (2,6), the light source (24) is arranged towards the inside, and wherein the photoelectric sensor (22) is arranged towards the outside on the side opposite to the light source (24).

9. The device according to claim 1 wherein a weight (14) is attached to the single fiber (1) to generate pretension for testing.

10. The device according to claim 18 further including a draw-off clamp (4) with simultaneous measurement of tensile force for adjusting the pretension on the single fiber (1), by adjusting the length of the single fiber (1) in the tensile zone.

* * * * *